(12) United States Patent
Gondek et al.

(10) Patent No.: US 10,395,008 B2
(45) Date of Patent: Aug. 27, 2019

(54) DEVICE CONNECTIVITY ENGINE

(71) Applicant: Welch Allyn, Inc., Skaneateles Falls, NY (US)

(72) Inventors: Cory R. Gondek, Tigard, OR (US); Soundharya Nagasubramanian, Portland, OR (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 1090 days.

(21) Appl. No.: 14/723,593

(22) Filed: May 28, 2015

(65) Prior Publication Data

US 2016/0350504 A1    Dec. 1, 2016

(51) Int. Cl.
*G06F 19/00* (2018.01)
*G06Q 50/24* (2012.01)
*G06Q 10/10* (2012.01)

(52) U.S. Cl.
CPC ......... *G06F 19/3418* (2013.01); *G06Q 10/10* (2013.01); *G06Q 50/24* (2013.01)

(58) Field of Classification Search
None
See application file for complete search history.

(56) References Cited

U.S. PATENT DOCUMENTS

| | | |
|---|---|---|
| 6,416,471 B1 | 7/2002 | Kumar et al. |
| 7,353,063 B2 | 4/2008 | Simms, Jr. |
| 7,384,410 B2 | 6/2008 | Eggers et al. |
| 7,689,439 B2 * | 3/2010 | Parker .............. G06Q 50/22 705/2 |
| 7,926,065 B2 | 4/2011 | Meadows et al. |
| 8,065,161 B2 | 11/2011 | Howard et al. |
| 8,533,746 B2 | 9/2013 | Nolan et al. |
| 2001/0029509 A1 | 10/2001 | Smith et al. |

(Continued)

FOREIGN PATENT DOCUMENTS

| | | |
|---|---|---|
| EP | 0537936 A1 | 4/1993 |
| KR | 10-2012-0091209 A | 8/2012 |

OTHER PUBLICATIONS

Philips Suresigns VS4 Vital Signs Monitor Owners Manual, Release A.04, 2012.

(Continued)

*Primary Examiner* — Michael Tomaszewaki
(74) *Attorney, Agent, or Firm* — Merchant & Gould P.C.

(57) ABSTRACT

An example medical device includes a physiological measurement device and a computing device. The computing device includes a device management engine and a data connectivity engine. The device management engine is configured to receive data captured by the physiological measurement device. The data captured by the physiological measurement device is formatted in a first data format. The device connectivity engine is further configured to transform the data captured by the physiological measurement device into an array of key-value pairs. The device connectivity engine is further configured to populate a template with at least some of the values from the key-value pairs to generate a populated template. The populated template includes at least a portion of the data captured by the physiological measurement device in a second data format. The device connectivity engine is further configured to transmit the populated template.

18 Claims, 8 Drawing Sheets

(56) References Cited

U.S. PATENT DOCUMENTS

| | | |
|---|---|---|
| 2005/0228693 A1 | 10/2005 | Webb et al. |
| 2009/0036750 A1 | 2/2009 | Weinstein et al. |
| 2009/0063193 A1 | 3/2009 | Barton et al. |
| 2010/0076783 A1* | 3/2010 | Mathur ............... G06F 21/6245 705/2 |
| 2010/0153228 A1 | 6/2010 | Ahmavaara |
| 2010/0250280 A1 | 9/2010 | Sutherland |
| 2011/0087652 A1* | 4/2011 | Westin ................. G06F 19/321 707/722 |
| 2011/0093510 A1 | 4/2011 | Beck et al. |
| 2011/0295082 A1* | 12/2011 | Craw .................. G06F 19/3418 600/301 |
| 2013/0110547 A1 | 5/2013 | Englund et al. |
| 2013/0132109 A1 | 5/2013 | Mruthyunjaya et al. |
| 2013/0150686 A1 | 6/2013 | Fronterhouse et al. |
| 2013/0151285 A1* | 6/2013 | McLaren .............. G06F 3/0484 705/3 |
| 2013/0204450 A1 | 8/2013 | Kagan et al. |
| 2014/0108025 A1 | 4/2014 | Echeverria Cabrera et al. |

OTHER PUBLICATIONS

PCT International Search Report and Written Opinion in PCT/US2016/034311, dated Sep. 7, 2016, 11 pages.

\* cited by examiner

DEVICE CONNECTIVITY ENGINE

INTRODUCTION

Medical devices may be used in healthcare environments, such as hospitals and clinics, to measure and monitor physiological parameters of patients. For example, some medical devices may be used to measure vital signs of a patient. Health information systems are also used in healthcare environments to record various information about patients. Health information systems may store biographical data about patients and historical records related to the patients. Healthcare environments often include other servers as well, such as user authentication servers.

SUMMARY

In one aspect, a medical device, comprising: a physiological measurement device; and a computing device comprising: a device management engine configured to receive data captured by the physiological measurement device, wherein the data captured by the physiological measurement device is formatted in a first data format; and a device connectivity engine configured to: transform the data captured by the physiological measurement device into an array of key-value pairs; populate a template with at least some values from the array of key-value pairs to generate a populated template, wherein the populated template includes at least a portion of the data captured by the physiological measurement device in a second data format; and transmit the populated template.

In another aspect, a method of facilitating data communication between a medical device and a server, the method comprising: receiving, by the medical device, data captured by a physiological measurement device of the medical device, wherein the data captured by the physiological measurement device is formatted in a first data format; transforming the data captured by the physiological measurement device into an array of key-value pairs; populating a template with at least some values from the array of key-value pairs to generate a populated template, wherein the populated template includes at least a portion of the data captured by the physiological measurement device in a second data format; and transmitting the populated template to the server.

In yet another aspect, a medical device, comprising: a physiological measurement device; and a computing device comprising: a device management engine configured to receive data captured by the physiological measurement device, wherein the data captured by the physiological measurement device is formatted in a first data format; and a device connectivity engine configured to: listen to a TCP/IP port for communication from the device management engine; receive, via the TCP/IP port, the data captured by the physiological measurement device; identify a script program from the plurality of script programs stored in a cache; and execute the script program, causing the device connectivity engine to: transform the data captured by the physiological measurement device into an array of key-value pairs, wherein keys of the array of key-value pairs are generic key values and at least some of the values of the array of key-value pairs are generated by performing a conversion operation on at least a portion of the data captured by the physiological measurement device; populate a template with at least some of the values from the array of key-value pairs to generate a populated template, wherein the populated template includes at least a portion of the data captured by the physiological measurement device in a second data format; and transmit the populated template to an external server.

DETAILED DESCRIPTION

Figure 1:
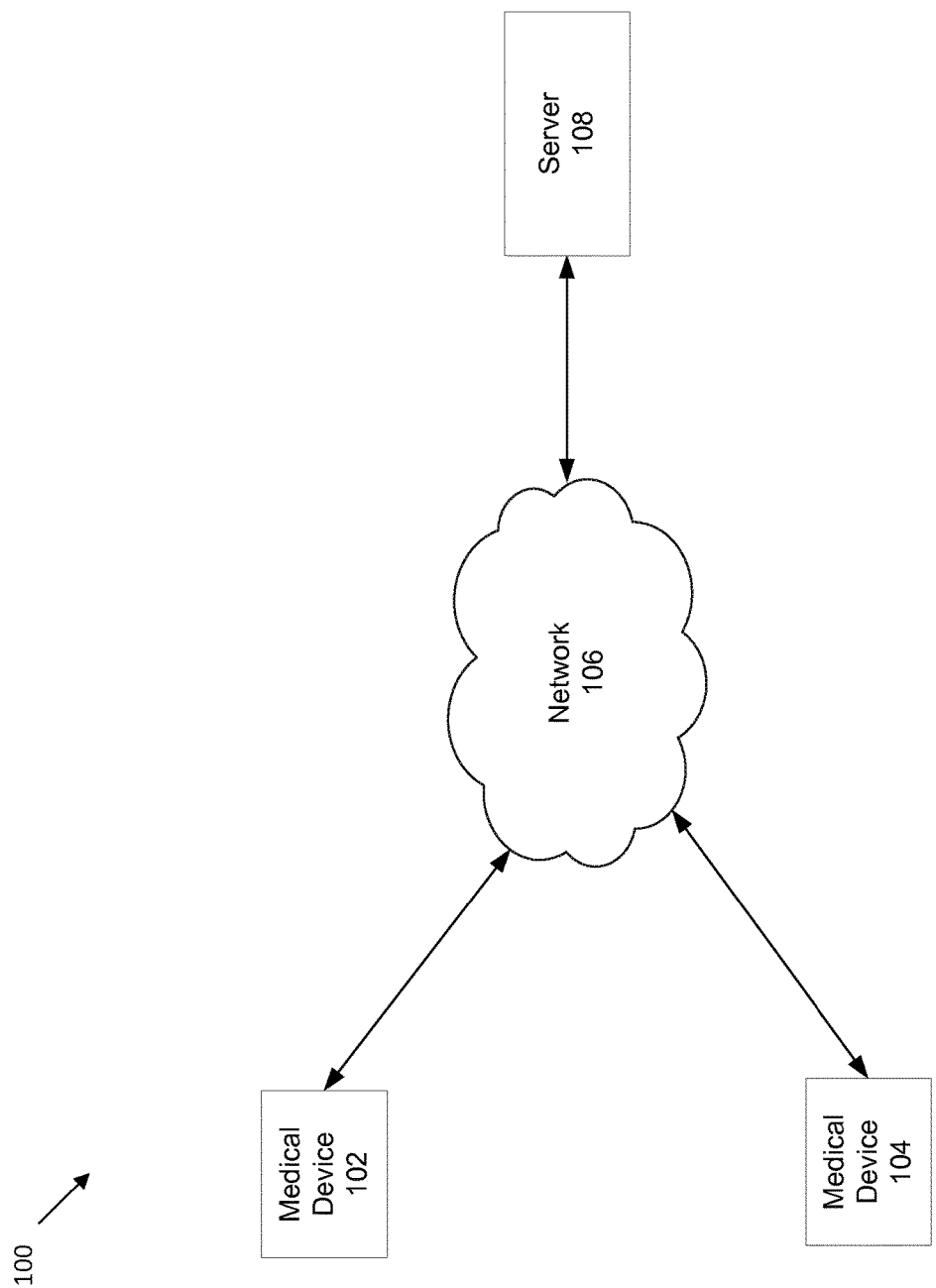
FIG. 1 shows a block diagram of an example system for communicating between medical devices and servers.

Medical devices may implement one or more communication protocols to facilitate communication with external devices or servers. There are many communication protocols that may be implemented by various medical device and servers. One example communication protocol is the Welch Allyn Communications Protocol (WACP). Other example protocols include various Health Level 7 (HL7) protocols. WACP and the HL7 protocols are just a few examples of communication protocols, and medical devices and servers may implement other communication protocols as well.

Health care providers or patients may benefit from communication between medical devices and various servers. For example, it may be beneficial to store a measurement of a physiological parameter of a patient captured by a medical device in an electronic health record associated with the patient that is stored on a health information system (HIS) server. Additionally, it may be beneficial to alert a billing server of various measurements that have been taken using a medical device in order to facilitate billing and collecting payments for the measurement. The foregoing are just examples. There are, of course, many other servers that perform many other functions with which it may be beneficial for a medical device to communicate.

As mentioned previously, there are many different communication protocols. In order to facilitate communication, a medical device may implement a communication protocol used by a target device or server. Alternatively, a translation process may be used to translate messages in a communication protocol understood by the medical device to a communication protocol understood by the server.

In some embodiments, the medical device includes a device connectivity engine that facilitates communication between the medical device and one or more external servers. The device connectivity engine may receive data from one or both of the medical device and the one or more external servers. Data from the medical device may be formatted in a medical-device specific format using a communications protocol of the medical device. Conversely, data from the external servers may be formatted in a different format that is specified by an application running on the external server. After receiving the data, the device connectivity engine transforms the data appropriately for its destination (i.e., the medical device or the external server) and transmits the transformed data to the destination.

In some embodiments, the medical device communicates with the device connectivity engine by transmitting data to a listener engine via a particular TCP/IP port on the medical device. Beneficially by communicating with the listener engine over a TCP/IP port, the process used by the medical device is nearly identical whether it is being used to communicate with the device connectivity engine or an external component that translates data. For example, in some embodiments, a configuration parameter that specifies an IP address for outgoing data can be used to control whether the medical device transmits data to an internal device connectivity engine or an external data translation tool.

Additional benefits of the device connectivity engine include that the templates can be configured to format messages to the requirements of many different types of external servers without requiring modifications to the external servers. Additionally, the medical devices do not need to adopt a new data format in order to communicate with external servers that have particular data formatting requirements. Instead, the outgoing data is routed through the device connectivity engine to perform the data transformation rather than being sent directly to its destination. In this manner, devices that operate using existing or legacy communication protocols can interact with servers that do not support those communication protocols with minimal change (e.g., the addition of the device connectivity engine).

FIG. 1 is a block diagram illustrating an example system 100 for communicating between medical devices and servers. The system 100 includes medical device 102 and 104, network 106, and server device 108.

In this example, the medical devices 102, 104 are used to collect physiological data from patients. As used herein, "medical device" refers to any device that can be used in a medical environment. Examples of medical devices include, but are not limited to, thermometers, blood pressure sensors, heart rate sensors, pulse rate sensors, SpO2 sensors, devices to monitor vital signs, devices for measuring body weight, devices for metering fluids, etc. These medical devices can be located in a medical environment. Medical environments, such as clinics, hospitals, nursing homes, care facilities, and at-home care stations, can rely on peripheral devices that communicate, display, and coordinate the monitoring and maintenance of a patient's health. In one example, the medical devices 102, 104 are located in the same medical environment. In another example, the devices are located in different medical environments that are spread out geographically.

The medical devices 102, 104 communicate using the network 106. In one example, the medical devices 102, 104 and the network 106 are part of a CONNEX™ system from Welch Allyn of Skaneateles Falls, N.Y., although other systems can be used. In such an example, the medical devices 102, 104 communicate through known protocols, such as the Welch Allyn Communications Protocol (WACP). WACP uses a taxonomy as a mechanism to define information and messaging. Taxonomy can be defined as description, identification, and classification of a semantic model. Taxonomy as applied to a classification scheme may be extensible. Semantic class-based modeling utilizing taxonomy can minimize the complexity of data description management by limiting, categorizing, and logically grouping information management and operational functions into families that contain both static and dynamic elements.

The network 106 is an electronic communication network that facilitates communication between the medical devices 102, 104 and the server device 108. An electronic communication network is a set of computing devices and links between the computing devices. The computing devices in the network use the links to enable communication among the computing devices in the network. The network 106 can include routers, switches, mobile access points, bridges, hubs, intrusion detection devices, storage devices, stand-alone server devices, blade server devices, sensors, desktop computers, firewall devices, laptop computers, handheld computers, mobile telephones, and other types of computing devices.

In various embodiments, the network 106 includes various types of links. For example, the network 106 can include wired and/or wireless links. Furthermore, in various embodiments, the network 106 is implemented at various scales. For example, the network 106 can be implemented as one or more local area networks (LANs), metropolitan area networks, subnets, wide area networks (such as the Internet), or can be implemented at another scale.

In this example, the medical devices 102, 104, and the network 106 are all part of the same network. In other words, the medical devices 102, 104 and the network 106 communicate with one another over a LAN behind a wall safeguarding the devices from outside influences on the Internet, such as a firewall.

The medical devices 102, 104 can provide various types of functionality, including measuring or monitoring patient physiological parameters. The medical devices 102, 104 can include one or more physiological monitor devices configured to measure and possibly display representations of one or more physiological parameters of a patient. In addition, the medical devices 102, 104 can include one or more desktop, laptop, or wall-mounted devices. In some embodiments, the medical devices 102, 104 are configured to be used by a clinician to monitor the physiological parameters of multiple patients at one time. Such monitor devices are typically not wall mounted.

The medical devices 102, 104 can communicate with each other through the network 106. In various embodiments, the medical devices 102, 104 can communicate various types of data with each other through the network 106. For example, in embodiments where the medical devices 102, 104 include a set of physiological monitor devices and a separate monitor device, each of the physiological monitor devices can send data representing measurements of physiological parameters of patients to the monitor device. In this way, the medical devices 102, 104 can display representations of physiological parameters to a clinician.

The medical devices 102, 104 can send various types of data and can receive various types of data through the network 106. For example, in some embodiments, the medical devices 102, 104 can send measurements of physiological parameters. In another example, the medical devices 102, 104 can retrieve past measurements of physiological parameters of patients.

The server device 108 communicates through the network 106 with the medical devices 102, 104. In this example, the server device 108 receives, stores, and associates physiological parameters measured by the medical devices 102, 104 with patient records. In some embodiments, the server device 108 includes a health information system, such as a system that captures, stores, manages or transmits information related to the health, including healthcare information, of individuals or organizations that provide health and healthcare services. Examples of health information systems include electronic medical records (EMR) systems and electronic health record (EHR) systems. In some embodiments, the server communicate through known protocols, such as the Welch Allyn Communications Protocol (WACP).

In some embodiments, the server device 108 is located "in the cloud." In other words, the server device 108 is located outside of the internal network associated with the medical devices 102, 104. In such examples, the server device 108 may not communicate directly with the medical devices 102, 104 but may instead communicate with a central server located within the same network as the medical devices 102, 104 such as the CONNEX™ system from Welch Allyn of Skaneateles Falls, N.Y. Intermediary servers in the CONNEX™ system, in turn, communicate with the medical devices 102, 104. Alternatively, the medical devices 102, 104 communicate directly with the server device 108 even if the server is located outside of the internal network associated with the medical devices 102, 104.

The medical devices 102, 104 and the server device 108 include computing systems. As used herein, a computing system is a system of one or more computing devices. A computing device is a physical, tangible device that processes data. Example types of computing devices include personal computers, standalone server computers, blade server computers, mainframe computers, handheld computers, smart phones, special purpose computing devices, and other types of devices that process data. In addition to the computing systems, the medical devices 102, 104 may include special purpose components that operate to capture various physiological or other parameters. Further, the computing systems included in the medical devices 102, 104 may include special-purpose components that are configured to interact with the special-purpose components.

Figure 2:
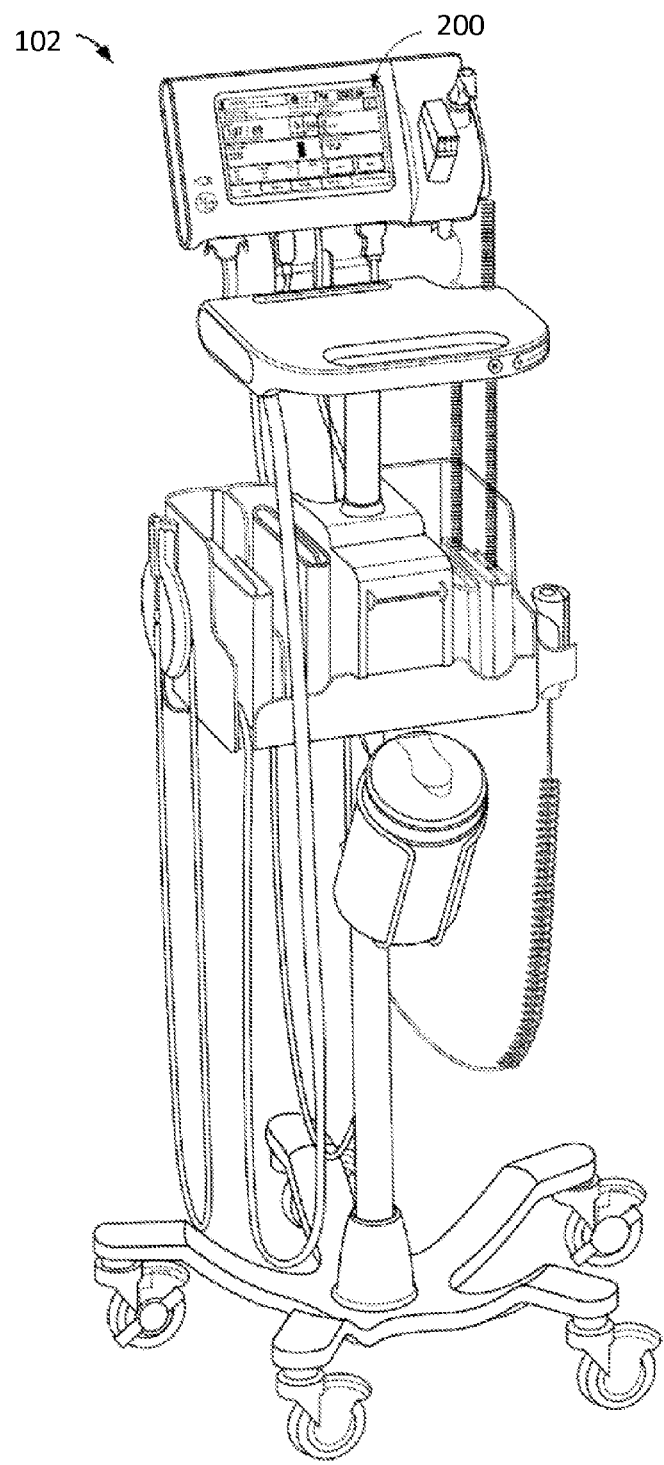
FIG. 2 illustrates an example medical device of FIG. 1.

FIG. 2 illustrates one example of the medical device 102. The medical device 102 is shown on a mobile cart, and the medical device 102 is programmed to provide the functionalities described herein. The medical device 102 includes a display screen 200 and one or more physiological measurement devices that are configured to measure one or more physiological parameters of a health-care recipient, also referred to herein as a patient. The display screen 200 operates to display information. In some embodiments, the display screen 200 is a touch-sensitive display screen and operates to receive input from users. Some embodiments include additional or alternative input devices for receiving input from users. Other embodiments can include more or fewer components than those shown in FIG. 2, or can include different components that accomplish the same or similar functions.

The medical device 102 is able to operate within one or more profiles. A profile is a series of one or more tasks that a user of the medical device 102 performs. When the medical device 102 operates within a profile, the medical device 102 provides functionality suitable for assisting the user in performing the profile. When the medical device 102 operates within different profiles, the medical device 102 provides different functionality.

When the medical device 102 is manufactured, the medical device 102 is configured to be able to operate within one or more profiles. After the medical device 102 is manufactured, the medical device 102 can be reconfigured to operate within one or more additional profiles. In this way, a user can adapt the medical device 102 for use in different profiles as needed.

In various embodiments, the medical device 102 operates within various profiles. For example, in some embodiments, the medical device 102 can operate within an interval profile or a non-interval profile. Example types of non-interval profiles include, but are not limited to, a spot check profile and an office profile.

In example embodiments, the names for the profiles can be defined by the user. For example, the user can rename an "interval profile" as "ED 3 North" or any other nomenclature as desired to provide more context to the user.

When the medical device 104 is operating within the interval profile, the medical device 104 obtains a series of measurements of one or more physiological parameters of a single monitored patient over a period of time. In addition, the medical device 104 displays, on the display screen 200, an interval profile home screen. The interval profile home screen contains a representation of a physiological parameter of the monitored patient. The representation is based on at least one measurement in the series of measurements. A representation of a physiological parameter is a visible image conveying information about the physiological parameter.

For example, when the medical device 104 is operating within the interval profile, the medical device 104 can obtain a blood pressure measurement of a single patient once every ten minutes for six hours. In this example, the medical device 104 displays an interval profile home screen that contains a representation of the patient's blood pressure based on a most recent one of the blood pressure measurements. In this way, a user of the medical device 104 can monitor the status of the patient.

When the medical device 104 is operating within a non-interval profile, the medical device 104 obtains a measurement of one or more physiological parameters from each patient in a series of patients. In addition, the medical device 104 displays a non-interval profile home screen on the display screen 200. The non-interval profile home screen contains a representation of the physiological parameter of a given patient in the series of patients. The representation is based on the measurement of the physiological parameter of the given patient.

In one example, when the medical device 104 is operating within a spot check profile, the medical device 104 obtains blood pressure measurements from a series of previously-identified patients. In this other example, the medical device 104 displays a spot check profile home screen containing a blood pressure measurement of a given patient in the series of previously-identified patients. In this way, a user of the medical device 104 can perform spot checks on the blood pressures of patients who have already been admitted to a hospital.

As used in this document, a patient is a previously identified patient when the medical device 104 stores information regarding the identity of the patient. In another example, when the medical device 104 is operating within an interval profile, the medical device 104 can obtain a single blood pressure measurement from each patient in a series of unidentified patients as the patients arrive at a hospital.

The interval profile home screen may be different than the non-interval profile home screen. Further, as discussed below, the navigation options associated with the different profiles allows for efficient monitoring based on the environment in which the device is used. In various embodiments, the interval profile home screen is different than the non-interval profile home screen in various ways. For example, in some embodiments, the interval profile home screen includes at least one user-selectable control that is not included in the non-interval profile home screen. In other embodiments, a representation of a physiological parameter in the interval profile home screen has a different size than a representation of the same physiological parameter in the non-interval profile home screen.

Figure 3:
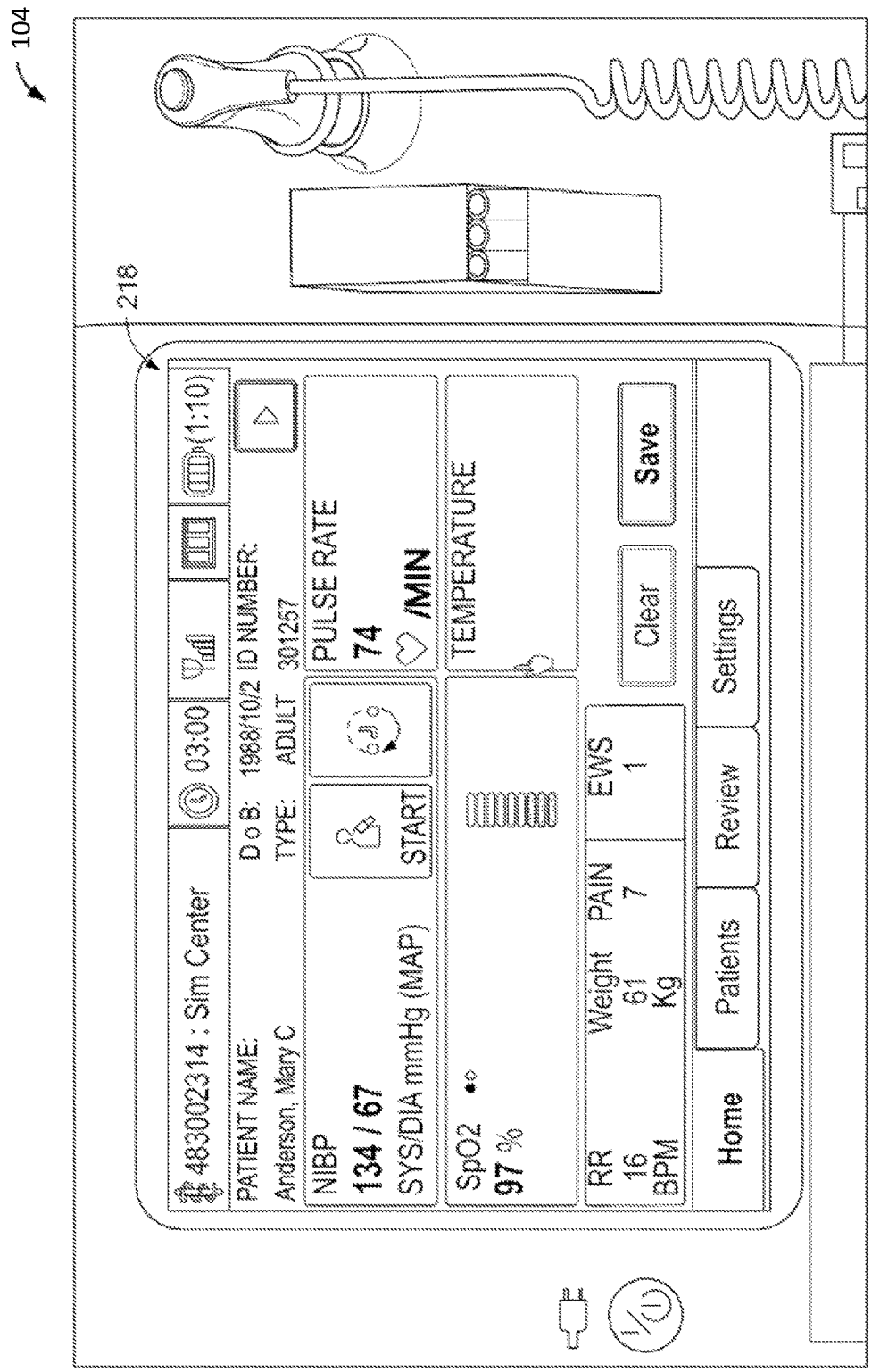
FIG. 3 illustrates another example medical device of FIG. 1.

FIG. 3 illustrates one example of the medical device 104. In this example, the medical device 104 is similar to the medical device 102 described above. The medical device 104 is configured to be mounted on a wall and may also be programmed in a manner similar to that described above to monitor physiological parameters of a patient. Additionally, in some embodiments, the medical devices 102, 104 are stand-alone devices, which can mean that the medical devices 102, 104 are not part of a mobile cart or wall-mounted station.

In the examples described herein, the medical devices 102, 104 are computing devices that have been programmed to perform special, complex functions. These specially-programmed devices function to capture physiological measurements and transmit those physiological measurements to various external servers with greater efficiency.

The medical devices 102, 104 shown in FIGS. 2 and 3 are only examples of a medical device. In some examples described herein, the medical devices 102, 104 are portable devices. In other examples, the medical devices 102, 104 are non-portable devices, such as computing devices like workstations. All different types of medical devices used to collect patient data can be used. Many configurations are possible.

Figure 4:
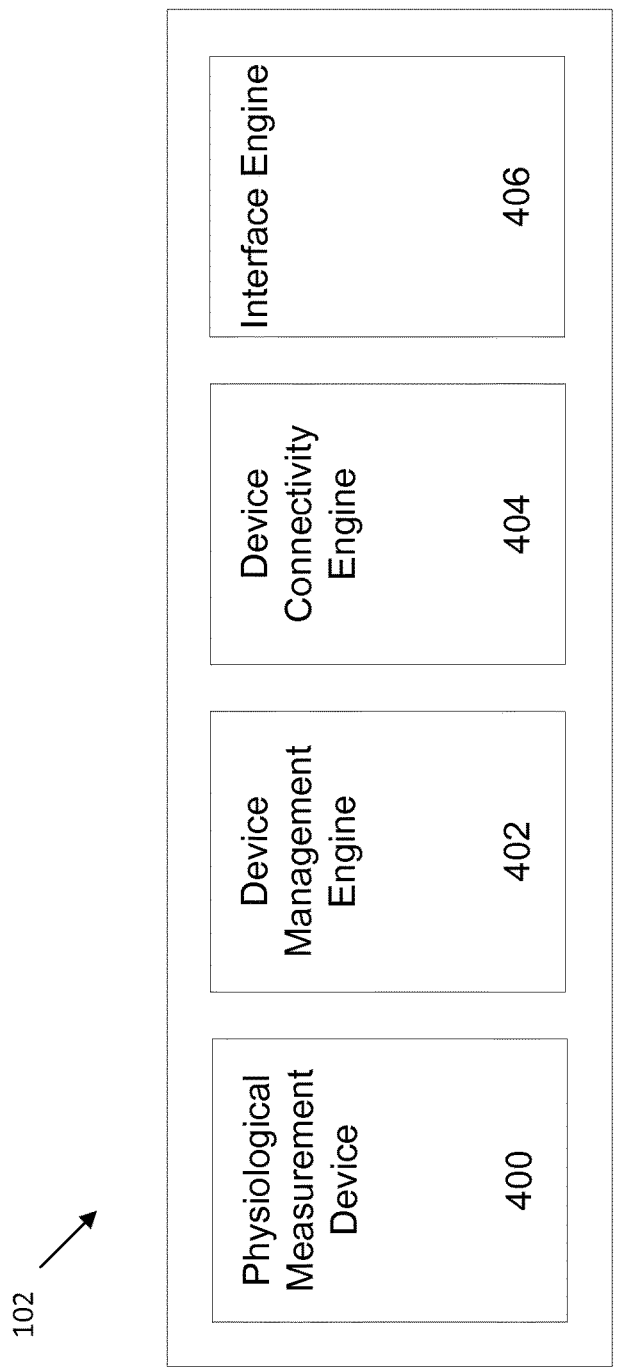
FIG. 4 illustrates a block diagram of an example medical device of FIG. 1.

FIG. 4 is a block diagram illustrating example logical components of the medical device 102. The medical device 102 includes a physiological measurement device 400, a device management engine 402, a device connectivity engine 404, and an interface engine 406.

The physiological measurement device 400 operates to measure one or more physiological parameters of a patient. Some embodiments include multiple physiological measurement devices.

An example physiological measurement device is an SpO2 measurement device. The SpO2 measurement device is designed to measure oxygen content within the blood of a patient. In some embodiments, the SpO2 measurement device includes a clip that attaches to an appendage of a patient, such as a finger. The clip is designed to detect and measure a pulse and an oxygen content of blood flowing within the patient.

Another example physiological measurement device is a non-invasive blood pressure (NIBP) measurement device. The NIBP measurement device is designed to measure blood pressure of a patient. In some embodiments, the NIBP device includes an inflatable cuff that attaches to an appendage of a patient, such as an upper arm of the patient. The inflatable cuff is designed to measure the systolic and diastolic blood pressure of the patient, the mean arterial pressure (MAP) of the patient, and the pulse rate of blood flowing within the patient.

Another example physiological measurement device is a temperature measurement device. The temperature measurement device is designed to measure the body temperature of a patient. In some embodiments, the temperature measurement device includes a handle and a temperature probe. The probe is designed to make physical contact with a patient in order to sense a body temperature of the patient. In some embodiments, the temperature probe is removable.

The device management engine 402 operates to manage the physiological measurement device 400. In some embodiments, the device management engine 402 transmits various control signals to the physiological measurement device 400 to activate or deactivate the physiological measurement device 400. Additionally, in some embodiments, the device management engine 402 operates to receive data captured by the physiological measurement device 400 and cause the received data to be stored. In some embodiments, the device management engine 402 transmits data captured by the physiological measurement device to the device connectivity engine 404 via a listening port on the medical device 102. In some embodiments, the device management engine 402 transmits data that is formatted in a binary format used by the physiological measurement device 400. In some embodiments, the device management engine 402 is integral with the physiological measurement device 400.

The device connectivity engine 404 operates to transform and transmit data captured by the physiological measurement device to the server device 108. The device connectivity engine 404 is described in greater detail throughout, including with respect to FIGS. 6-9.

The interface engine 406 operates to generate a user interface for display on the display screen and to receive inputs from users. In some examples, the user interface displays various information about the patient, including data related to physiological measurements captured by the physiological measurement device 400. Additionally, some embodiments display additional information about the patient that is received from the server device 108, such as previously captured physiological measurement values.

Figure 5:
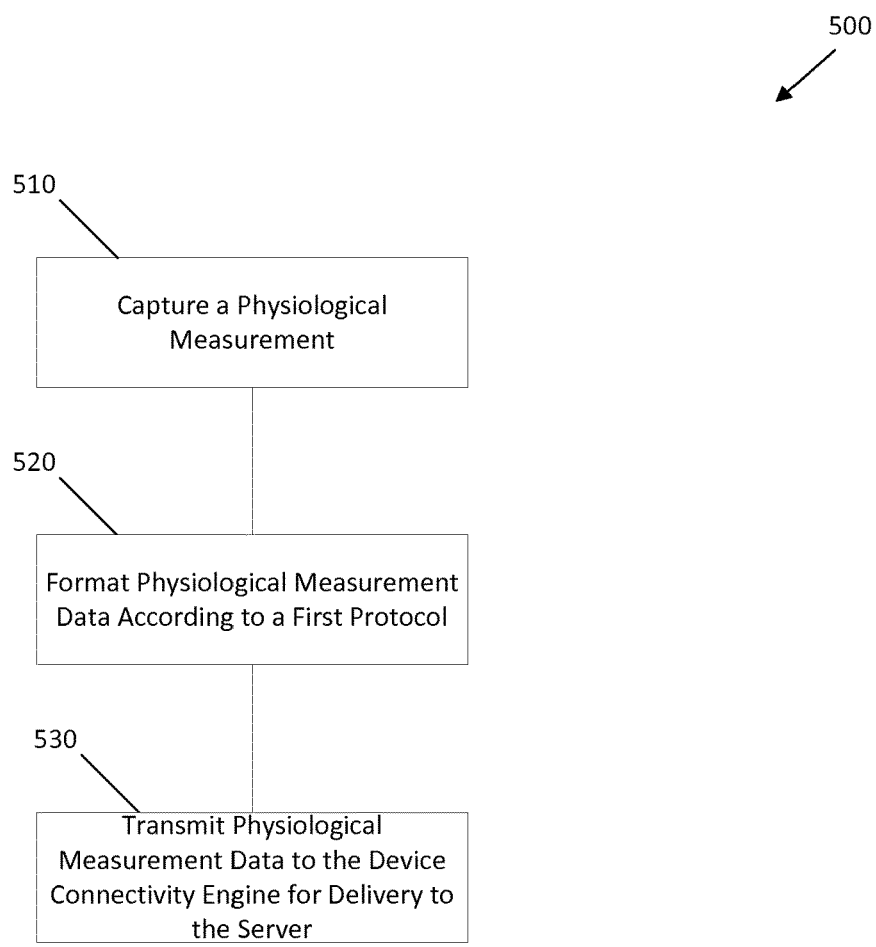
FIG. 5 illustrates an example process to transmit data to the device connectivity engine of FIG. 4.

Referring now to FIG. 5, an example process 500 performed by some embodiments of the medical devices 102, 104 is shown. The process operates to transmit data to the device connectivity engine.

At operation 510, a physiological measurement is captured using the physiological measurement device 400. The physiological measurement may be a single measurement or a series of measurements. In some embodiments, the physiological measurement is associated with a timestamp corresponding to the time the measurement was captured. Additionally, in some embodiments, the physiological measurement is associated with various additional data, such as parameters used while capturing the physiological measurement.

At operation 520, the physiological measurement data is formatted according to a first protocol. In some examples, the physiological measurement data is formatted according to a medical-device specific format. Examples of a medical-device specific format include device-specific variants of WACP. Additionally, in some embodiments, the physiological measurement data are stored in a binary format.

At operation 530, the physiological measurement data is transmitted to the device connectivity engine 404 for delivery to the server device 108. In some embodiments, the physiological measurement data is transmitted to the device connectivity engine 404 over a TCP/IP port on the medical devices 102, 104.

Figure 6:
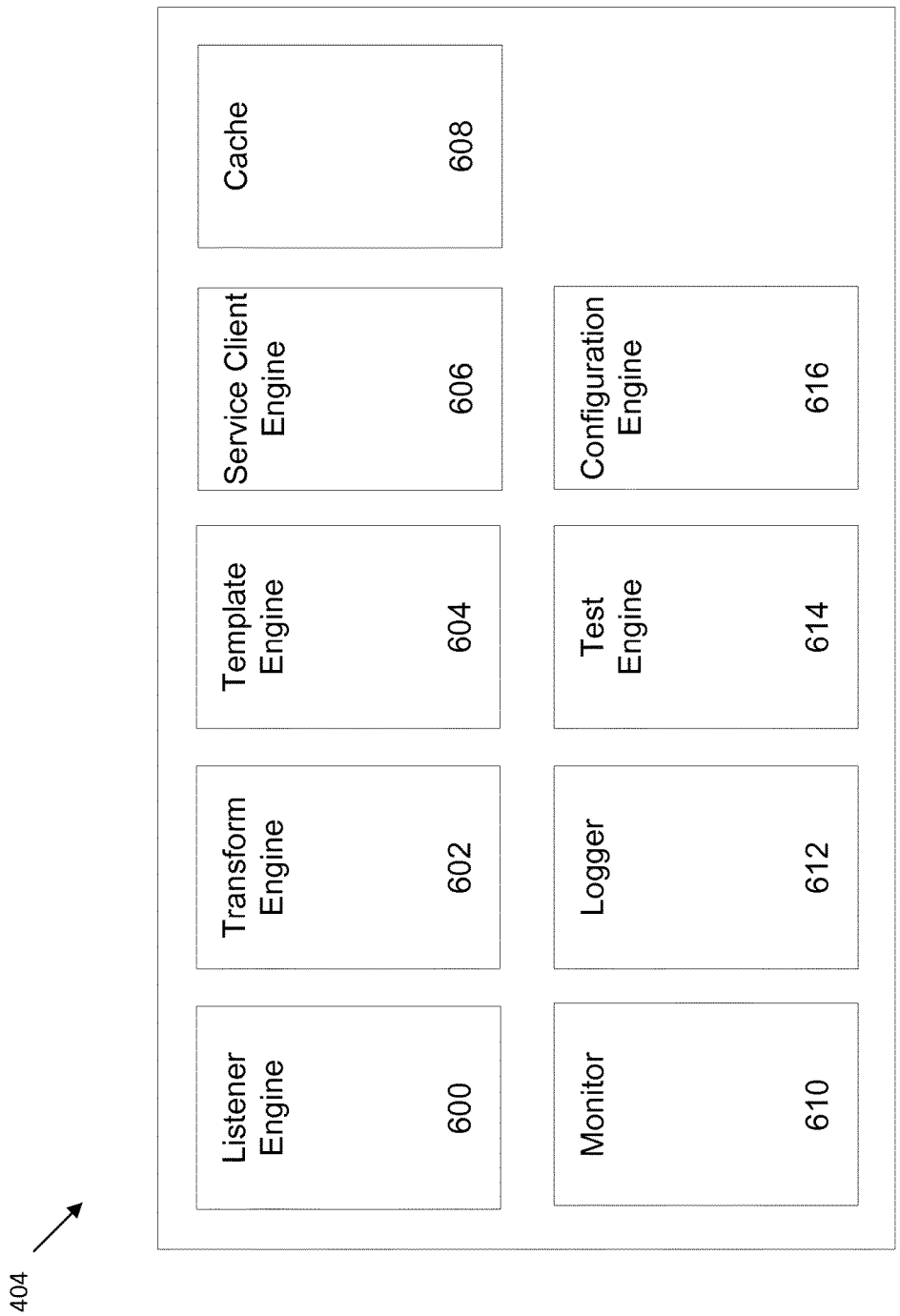
FIG. 6 is a block diagram illustrating an example device connectivity engine of FIG. 4.

FIG. 6 is a block diagram illustrating an example device connectivity engine 404. The device connectivity engine 404 includes a listener engine 600, a transform engine 602, a template engine 604, a service client engine 606, a cache 608, a monitor 610, a logger 612, a test engine 614, and a configuration engine 616.

The listener engine 600 operates to listen for communication over one or more TCP/IP ports on the medical devices 102, 104 and to receive data over those one or more ports. In some examples, the listener engine 600 listens to a first port for communication from the device management engine 402 and a second port for communication from the server device 108. In other embodiments, the listener engine 600 listens to one or more ports for communication from either the device management engine 402 or the server device 108. Additionally, in some embodiments, the listener engine 600 comprises multiple independent processes, including a first dedicated process for listening for communication from the device management engine 402 and a second dedicated process for listening for communication from the server device 108.

In some embodiments, the listener engine 600 determines the destination for the data that is received. For example, in some embodiments, the listener engine 600 determines that the medical device is the destination for data received from the server device 108 (e.g., for display using the interface engine 406 or for use in managing the physiological measurement device 400 by the device management engine 402). With respect to data received from the device management engine 402, in some embodiments, the listener engine 600 determines that the destination for the data is the server device 108. In embodiments that are configured to communicate with multiple external servers, the listener engine 600 may identify a particular destination server based on or more of configuration parameters, parameters provided by the device management engine with the data, or the content of the data. Other embodiments are possible as well.

In some embodiments, the listener engine 600 listens for Hypertext Transport Protocol (HTTP) requests that include a Universal Resource Locator (URL). The listener engine 600 may then parse the URL to determine a function that is being requested and parameters for that function. Beneficially, by listening for HTTP requests, the listener engine 600 may be able to receive requests from the server device 108 with no or minimal changes to the server device 108.

The transform engine 602 operates to transform data received by the listener engine 600 into another format. In some embodiments, the transform engine 602 selects a process for transforming the data based on the source of the data, the destination of the data, the content of the data, or the configuration of the device connectivity engine 404. The transformation process may include one or more of executing a program, including script programs, or calling a function. In some embodiments, the conversion process includes executing one or more script programs written in the PYTHON™ language (Python is a trademark of the Python Software Foundation of Delaware, USA). Other embodiments include script programs written in other languages.

In some embodiments, the transform engine 602 converts the received data to a generic (i.e., generally applicable) set of keys that are not specific to the sending medical device. For example, data related to body temperature readings may labelled as "Temp." by some of the sending medical devices. As an example, the data associated with the label "Temp." may be mapped to and stored with a key value of "Body Temperature." In order to convert the device-specific keys to generic keys, some embodiments of the transform engine 602 use a data definition file that is specific to the sending medical device to map each device-specific key to a generic key. Further, some embodiments additionally or alternatively use a database to store records that relate various keys to one another to convert device-specific keys to generic keys.

In some embodiments, the transform engine 602 transforms the data into an array of key-value pairs. An example array of key-value pairs is shown in table 1 below.

TABLE 1

| Key | Value |
|---|---|
| "Diastolic Blood Pressure" | "80" |
| "Systolic Blood Pressure" | "120" |
| "Body Temperature" | "98.6" |
| "SpO2" | "98%" |
| ... | ... |

The key-value pairs shown in table 1 are just examples. Depending on the received data, the contents of the array of key-value pairs will vary. Additionally, there may be more or fewer key-value pairs than shown in table 1 depending on the circumstances. The array of key-value pairs may be stored in memory or may be stored in a file or database. Other embodiments are possible as well.

In some embodiments, the transform engine 602 also applies conversion operations to at least some of the values that are stored in the array. Example conversion operations include converting temperatures from Fahrenheit to Centigrade and vice versa, converting weights from kilograms to pounds and vice versa, and converting pressure from millimeters of mercury (mmHg) to kiloPascals (kPa) and vice versa. Other examples of conversion operations include converting between an encoded, enumerated list of values and corresponding textual values (e.g., 1 may be converted to "left arm," 2 may be converted to "right arm." etc.) and vice versa. As another example, some embodiments may include a conversion that involves a mathematical formula being applied to a received value. Other embodiments include additional or different conversion engines as well. In some embodiments, conversion operations are applied based on the required data format of the destination server. Additionally, some conversion operations are applied to any value received that is in a particular format regardless of the destination server.

Additionally, in some embodiments, the data received by the listener engine 600 may not include labels at all. Instead, the received data is formatted according to a data definition file that identifies the order or location of various data fields within the full data set. Some embodiments of the transform engine 602 read the data definition file to determine the location of relevant data fields. Further, in some embodiments, the transform engine 602 converts the values from a binary format to a character based format or vice versa. The data definition file for the data may be received by the listener engine 600 or may be stored in the cache 608.

The template engine 604 operates to format the transformed data into an appropriate format for its destination. In some embodiments, the template engine 604 operates to select an appropriate engine based on the destination for the data. In some embodiments, a template is a string containing various text and fields that are configured to be populated with specific values (e.g., the values in the key-value array prepared by the transform engine 602). Once populated, the templates generate data in a format that is acceptable to the data's destination, such as an character-delimited string, an extensible markup language (XML) formatted string, etc. In some embodiments, the templates are stored in individual files. In other embodiments, the templates are stored in the cache 608.

Additionally, in some embodiments, the template engine 604 also applies conversion operations (as described above with respect to the transform engine 602) to at least some of the values that are used to populate the fields in the template. For example, the template engine 604 may apply one or more conversion operations to convert values to a specific format or a specific unit of measurement that is expected (or required) by the destination for the data.

The service client engine 606 operates to send data that has been formatted appropriately by the template engine 604 to the data's destination. In some embodiments, the service client engine 606 identifies an appropriate service client for communicating with the destination for the data. In some embodiments, the service client engine 606 includes a plurality of service clients. The service clients are modules that operate to communicate with a particular type of server or device using a particular communications protocol. Example service clients include clients for HL7, remote procedure call (RPC), Lightweight Directory Access Protocol (LDAP), Simple Object Access Protocol (SOAP), Hypertext Transport Protocol (HTTP), and Transmission Control Protocol/Internet Protocol (TCP/IP). In some embodiments, the service clients are used in combination. For example, the HL7, RPC, LDAP, SOAP, and HTTP service clients use the TCP/IP service client in some embodiments. The service client engine 606 may determine the appropriate service client based on or more of configuration parameters, the destination of the data, and the content of the data. In some embodiments, the service client engine 606 transmits the data to its destination using the identified service client.

The cache 608 operates to store data definition files, script programs, templates, and other files or data that may be frequently accessed by the device connectivity engine 404. In some embodiments, the cache 608 operates using one or more of random access memory (RAM) and a file system local to the device connectivity engine 404.

The monitor 610 operates to monitor the operation of the device connectivity engine 404 and its components such as the listener engine 600. In some embodiments, the monitor 610 operates to start a process running the listener engine 600 if it detects that the listener engine 600 is not running.

The logger 612 operates to log the operations of the device connectivity engine 404. In some embodiments, the logger 612 logs all operations that are performed by the device connectivity engine 404. In other embodiments, the logger 612 operates to log only errors that occur. Yet other embodiments of the logger 612 log only those events that match a predefined criteria. In various embodiments, the logger 612 operates to log events to one or more files or database tables. Other embodiments are possible as well.

The test engine 614 operates to execute various tests of the functionality of the device connectivity engine 404. For example, in some embodiments, the test engine executes tests that transmit data to the device connectivity engine 404 and compare the results to a predefined expected result. In this manner, the test engine 614 can be used to verify the continued performance of the device connectivity engine 404 after certain files (e.g., templates) or configuration settings have been modified.

The configuration engine 616 operates to manage the configuration of the device connectivity engine 404. In some embodiments, the configuration engine 616 loads a site configuration from a file during the startup process of the device connectivity engine 404. The site configuration may include various parameters such as network time out values and a network address for the server device 108. Additionally, in some embodiments, the configuration engine 616 verifies that the files in the cache 608 are current. If any of the files are out-of-date, the configuration engine 616 may replace the out-of-date files with updated files.

Figure 7:
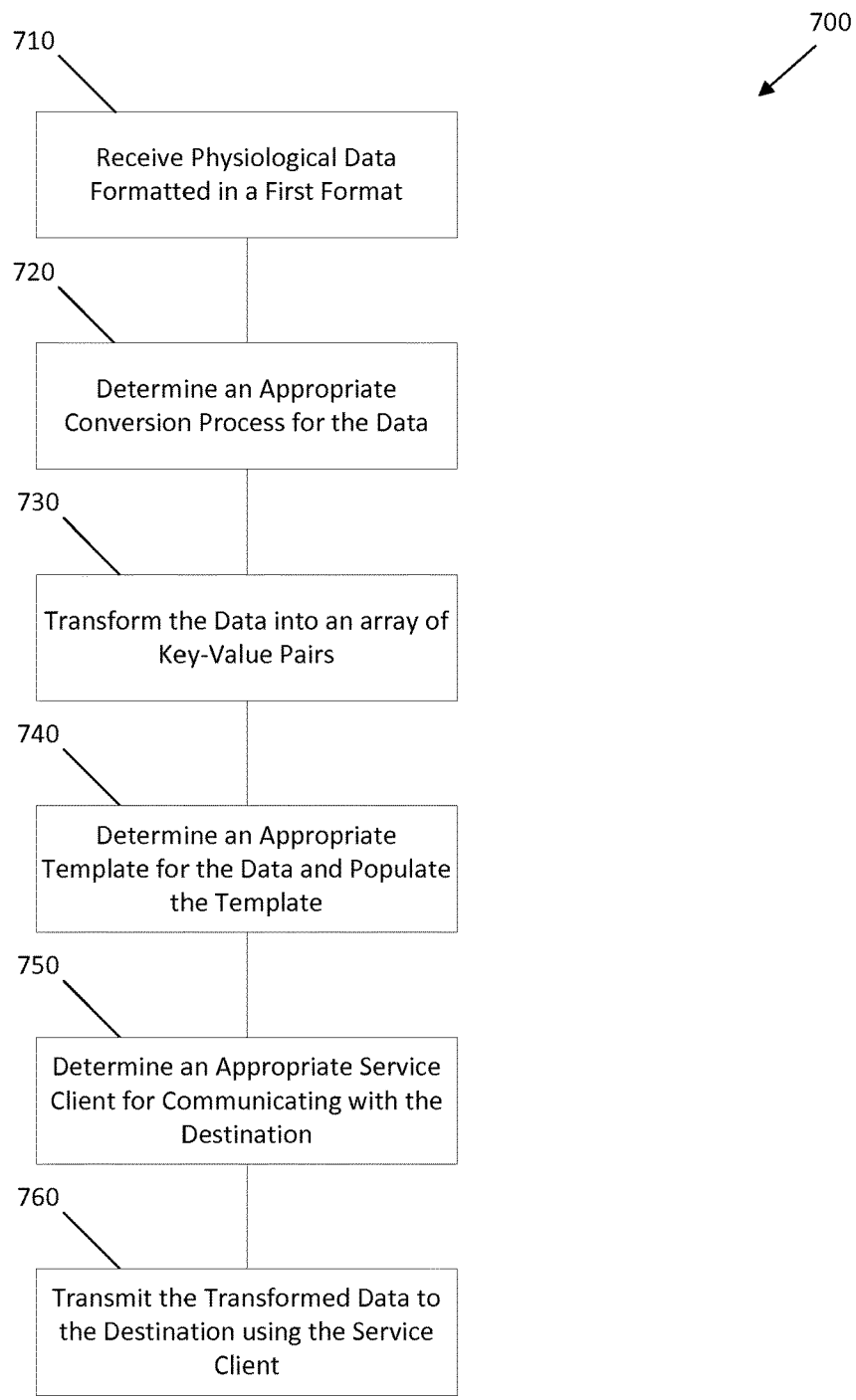
FIG. 7 illustrates an example process performed by some embodiments of the device connectivity engine of FIG. 4 to transform received data to an appropriate format for its destination.

Referring now to FIG. 7, an example process 700 performed by some embodiments of the device connectivity engine 404 is shown. The process 700 facilitates communication between the medical devices 102, 104 and the server device 108. The process 700 operates to transform received data to an appropriate format for its destination (e.g., the server device 108 or the medical devices 102, 104).

At operation 710, data is received in a first format. The data may be physiological data captured by the medical device. Alternatively, the data may be other data such as login/authentication information of a user, biographical data entered by a user of the medical device, or biographical or historical data stored in the server device 108. As discussed previously, the first format may be a device-specific format (if from the physiological measurement device 400) or an application-specific format (if from the server device 108). Alternatively, the first format may be a format defined by a communications protocol such as WACP or HL7.

At operation 720, an appropriate conversion process is determined for the received data based on, for example, the destination for the data, the source of the data, the content of the data, or the configuration of the device connectivity engine 404. Additionally, in some embodiments, the destination for the data is determined in operation 720 or at another point during process 700 based on the source of the data, the content of the data, or the configuration of the device connectivity engine 404.

At operation 730, the received data is transformed to an array of key-value pairs. In some embodiments, the keys of the key-value pairs are mapped to generic keys. Additionally, in some embodiments, various conversion operations (which have been described previously with respect to the transform engine 602) are applied to the received data to transform it.

At operation 740, an appropriate template is determined for the received data and the template is populated with the transformed data. In some embodiments, the appropriate template is determined based on one or more of the destination for the data, the source of the data, the content of the data, or the configuration of the device connectivity engine 404. In other embodiments, the template is determined based on the determined conversion process, which may specify a particular template. Additionally, in some embodiments, various conversion operations (which have been described previously with respect to the transform engine 602) are applied to the transformed data before the data is used to populate the template.

At operation 750, an appropriate service client is determined for communication with the destination for the data. In some embodiments, the appropriate service client is determined based on one or more of the destination for the data, the source of the data, the content of the data, or the configuration of the device connectivity engine 404. In other embodiments, the service client is determined based on the determined conversion process, which may specify a particular service client.

At operation 760, the template populated with the transformed physiological data is transmitted to the destination using the identified service client. Additionally, in at least some embodiments of the process 700, the device connectivity engine operates to receive a response from the destination. The response may include an acknowledgement, an indication of success or failure, or specific data. For example, in some embodiments, the medical devices 102, 104 may request certain information or records related to a patient from the server device 108. If the request succeeds, the server device 108 will return the requested information to the medical devices 102, 104 via the device connectivity engine 404. In some embodiments, the device connectivity engine may then perform process 700 on the response data received from the server device 108 to transform the response data for the medical devices 102, 104.

The process 700 can be used to perform various functions. For example, the process 700 can be used to transmit physiological data captured by the medical devices 102, 104 to an external health information system server; to receive return receipts from the external health information server acknowledging receipt of the physiological data; to receive and respond to a request for physiological data (e.g., vital signs) from an external health information server; to authenticate a user of the medical devices 102, 104 with an external LDAP server; to request and receive patient demographic data from an external health information system server; and to request and receive historical records for a patient from an external health information system server.

Figure 8:
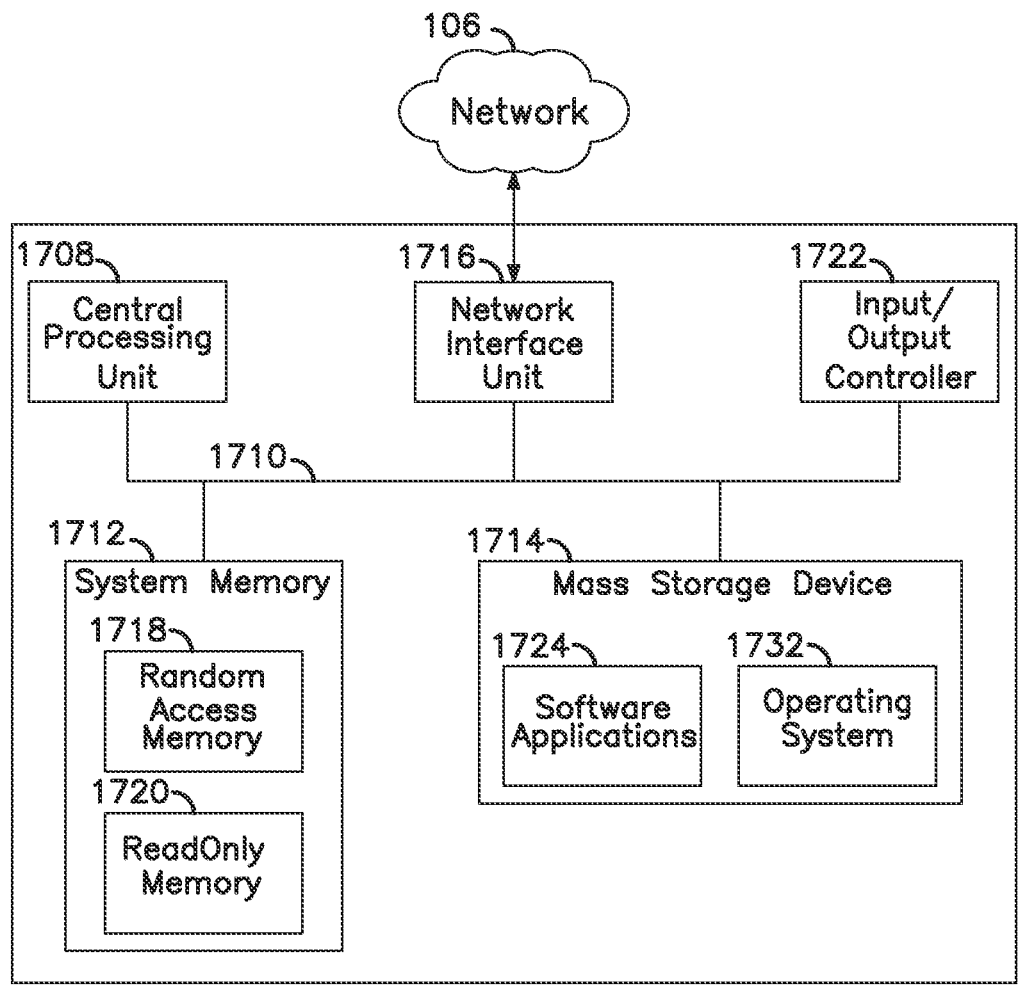
FIG. 8 illustrates example components of a medical device of the system of FIG. 1.

FIG. 8 illustrates example physical components of a computing device, such as the medical devices 102, 104. As illustrated, the device includes at least one central processing unit ("CPU") 1708, a system memory 1712, and a system bus 1710 that couples the system memory 1712 to the CPU 1708. The system memory 1712 includes a random access memory ("RAM") 1718 and a read-only memory ("ROM") 1720. A basic input/output system containing the basic routines that help to transfer information between elements within the device, such as during startup, is stored in the ROM 1720. The device further includes a mass storage device 1714. The mass storage device 1714 is able to store software instructions and data.

The mass storage device 1714 is connected to the CPU 1708 through a mass storage controller (not shown) connected to the system bus 1710. The mass storage device 1714 and its associated computer-readable data storage media provide non-volatile, non-transitory storage for the device. Although the description of computer-readable data storage media contained herein refers to a mass storage device, such as a hard disk or CD-ROM drive, it should be appreciated by those skilled in the art that computer-readable data storage media can be any available non-transitory, physical device or article of manufacture from which the device can read data and/or instructions.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the device.

According to various embodiments of the invention, the device may operate in a networked environment using logical connections to remote network devices through the network 106, such as a local network, the Internet, or another type of network. The device connects to the network 106 through a network interface unit 1716 connected to the system bus 1710. The network interface unit 1716 may also be utilized to connect to other types of networks and remote computing systems. The device also includes an input/output controller 1722 for receiving and processing input from a number of other devices, including a keyboard, a mouse, a touch user interface display screen, or another type of input device. Similarly, the input/output controller 1722 may provide output to a touch user interface display screen, a printer, or other type of output device.

As mentioned above, the mass storage device 1714 and the RAM 1718 of the device can store software instructions and data. The software instructions include an operating system 1732 suitable for controlling the operation of the device. The mass storage device 1714 and/or the RAM 1718 also store software instructions, that when executed by the CPU 1708, cause the device to provide the functionality of the device discussed in this document. For example, the mass storage device 1714 and/or the RAM 1718 can store software instructions that, when executed by the CPU 1708, cause the physiological monitor device to display the home screen and other screens.

Although the example medical devices described herein are devices used to monitor patients, other types of medical devices can also be used. For example, the different components of the CONNEX™ system, such as the intermediary servers that communicate with the monitoring devices, can also require maintenance in the form of firmware and software updates. These intermediary servers can be managed by the systems and methods described herein to update the maintenance requirements of the servers.

Embodiments of the present invention may be utilized in various distributed computing environments where tasks are performed by remote processing devices that are linked through a communications network in a distributed computing environment.

The block diagrams depicted herein are just examples. There may be many variations to these diagrams described therein without departing from the spirit of the disclosure. For instance, components may be added, deleted or modified.

While embodiments have been described, it will be understood that those skilled in the art, both now and in the future, may make various improvements and enhancements can be made.

What is claimed is:

1. A single medical device, comprising:
   a physiological measurement device of the single medical device to capture data associated with vital signs; and
   a computing device of the single medical device, comprising:
      a device management engine configured to receive the data captured by the physiological measurement device, wherein the data captured by the physiological measurement device is formatted in a first data format;
      a listener engine configured to determine a destination of the data sent by the single medical device; and
      a device connectivity engine configured to:
         transform the data captured by the physiological measurement device into an array of key-value pairs;
         identify a template from a plurality of templates based upon the destination for the data;
         populate the template with at least some values from the array of key-value pairs to generate a populated template, wherein the populated template includes at least a portion of the data captured by the physiological measurement device in a second data format; and
         transmit the populated template from the single medical device to the destination.

2. The medical device of claim 1, wherein the device connectivity engine is further configured to perform a conversion operation on at least a portion of the data captured by the physiological measurement device.

3. The medical device of claim 2, wherein the conversion operation is selected from a group of conversion operations comprising:
a temperature conversion operation that operates to convert between Fahrenheit and Celsius;
a weight conversion operation that operates to convert between kilograms and pounds; and
a pressure conversion operation that operates to convert between millimeters of mercury and kiloPascals.

4. The medical device of claim 1, wherein the first data format is a medical device-specific data format.

5. The medical device of claim 1, wherein the physiological measurement device operates to measure at least one of body temperature, SpO2, and blood pressure.

6. The medical device of claim 1, wherein the device connectivity engine includes a cache configured to store a plurality of script programs.

7. The medical device of claim 6, wherein the device connectivity engine identifies a script program from the plurality of script programs stored in the cache and executes the script program.

8. The medical device of claim 7, wherein the script program is identified at least in part based on the received data.

9. The medical device of claim 1, wherein the device connectivity engine includes a plurality of service clients and the device management engine is further configured to identify an appropriate service client from the plurality of service clients for use in transmitting the populated template.

10. The medical device of claim 9, wherein the plurality of service clients includes service clients for communication with an electronics medical records system.

11. The medical device of claim 1, wherein the device connectivity engine is configured to listen to a TCP/IP port for the data captured by the physiological measurement device.

12. A method of facilitating data communication between a single medical device and a server, the method comprising:
receiving, by the single medical device, data associated with vital signs captured by a physiological measurement device of the single medical device, wherein the data captured by the physiological measurement device is formatted in a first data format;
transforming the data captured by the physiological measurement device into an array of key-value pairs;
identifying a template from a plurality of templates based upon a destination for the data, the destination being the server;
populating the template with at least some values from the array of key-value pairs to generate a populated template, wherein the populated template includes at least a portion of the data captured by the physiological measurement device in a second data format; and
transmitting the populated template from the single medical device to the server.

13. The method of claim 12, further comprising performing a conversion operation on at least a portion of the data captured by the physiological measurement device.

14. The method of claim 13, wherein the conversion operation is selected from a group of conversion operations comprising:
a temperature conversion operation that operates to convert between Fahrenheit and Celsius;
a weight conversion operation that operates to convert between kilograms and pounds; and
a pressure conversion operation that operates to convert between millimeters of mercury and kiloPascals.

15. The method of claim 12, further comprising mapping at least some keys of the array of key-value pairs to generic keys.

16. The method of claim 12, further comprising listening to a TCP/IP port for the data captured by the physiological measurement device.

17. The method of claim 16, further comprising:
identifying a script program from a plurality of script programs stored in a cache; and
executing the script program.

18. A single medical device, comprising:
a physiological measurement device of the single medical device to capture data associated with vital signs; and
a computing device of the single medical device, comprising:
a device management engine configured to receive the data captured by the physiological measurement device, wherein the data captured by the physiological measurement device is formatted in a first data format; and
a device connectivity engine configured to:
listen to a TCP/IP port for communication from the device management engine;
receive, via the TCP/IP port, the data captured by the physiological measurement device;
identify a script program from the plurality of script programs stored in a cache; and
execute the script program, causing the device connectivity engine to:
transform the data captured by the physiological measurement device into an array of key-value pairs, wherein keys of the array of key-value pairs are generic key values and at least some of the values of the array of key-value pairs are generated by performing a conversion operation on at least a portion of the data captured by the physiological measurement device;
identify a template from a plurality of templates based upon a destination for the data, the destination being an external server associated storing an electronic health record;
populate a template with at least some of the values from the array of key-value pairs to generate a populated template, wherein the populated template includes at least a portion of the data captured by the physiological measurement device in a second data format; and
transmit the populated template from the single medical device to the electronic health record on the external server.

* * * * *